United States Patent
Mortisen et al.

(10) Patent No.: US 9,446,172 B2
(45) Date of Patent: Sep. 20, 2016

(54) MODIFICATION OF BIOABSORBABLE STENT TO REDUCE THROMBOGENECITY

(75) Inventors: Derek Mortisen, San Francisco, CA (US); Yunbing Wang, Sunnyvale, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 805 days.

(21) Appl. No.: 13/104,797

(22) Filed: May 10, 2011

(65) Prior Publication Data

US 2012/0290075 A1   Nov. 15, 2012

(51) Int. Cl.
*A61F 2/82* (2013.01)
*A61L 31/06* (2006.01)
*A61F 2/915* (2013.01)
*A61L 31/10* (2006.01)
*A61L 31/14* (2006.01)
*A61L 31/16* (2006.01)

(52) U.S. Cl.
CPC ............ *A61L 31/06* (2013.01); *A61F 2/915* (2013.01); *A61L 31/10* (2013.01); *A61L 31/148* (2013.01); *A61L 31/16* (2013.01); *A61F 2002/91575* (2013.01); *A61F 2210/0004* (2013.01); *A61F 2230/0054* (2013.01); *A61F 2250/0067* (2013.01); *A61L 2300/416* (2013.01); *A61L 2300/42* (2013.01)

(58) Field of Classification Search
CPC ........................................................ A61F 2/82
USPC ................... 623/1.38, 1.42, 1.43, 1.44, 1.46
See application file for complete search history.

(56) References Cited

U.S. PATENT DOCUMENTS

| | | | |
|---|---|---|---|
| 2006/0247761 A1* | 11/2006 | Greenberg | A61F 2/07 623/1.16 |
| 2007/0283552 A1 | 12/2007 | Gale et al. | |
| 2009/0012604 A1* | 1/2009 | Schmitz et al. | 623/1.42 |
| 2009/0324682 A1* | 12/2009 | Popowski | 424/426 |

OTHER PUBLICATIONS

Neuhhaus et al., "mTOR Inhibitors: An Overview", Liver Transpl. 7(6) pp. 473-484 (2001) (Review article).

* cited by examiner

*Primary Examiner* — Matthew Schall
(74) *Attorney, Agent, or Firm* — Squire Patton Boggs (US) LLP

(57) ABSTRACT

Bioabsorbable polymer scaffolds with coatings are disclosed that include immobilized antithrombotic agents on the scaffolds or in or on the coatings. The agents act synergistically with antiproliferative agents released from coatings by providing hemocompatibility during and without interfering with antiproliferative agent release. Methods of modifying scaffolds and coatings with the antithrombotic agents are disclosed.

10 Claims, 4 Drawing Sheets

MODIFICATION OF BIOABSORBABLE STENT TO REDUCE THROMBOGENECITY

BACKGROUND OF THE INVENTION

1. Field of the Invention

This invention relates to methods of treatment of coronary artery disease with bioabsorbable polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength around a circumferential direction of the stent.

Once expanded, the stent must adequately provide lumen support during a time required for treatment in spite of the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

The treatment of coronary artery disease with a stent may require the presence of the stent only for a limited period of time. During or part of this limited time a healing process takes place which includes changes in the structure of the vessel wall, referred to as remodeling. After the healing process is completed, the presence of the stent is no longer necessary.

Coronary stents made from biostable or non-erodible materials, such as metals, have become the standard of care for percutaneous coronary intervention (PCI) since such stents have been shown to be capable of preventing early and later recoil and restenosis. However, a stent made out of such biostable material retains is mechanical or structural integrity and remains at the implant site indefinitely unless it is removed by intervention or is dislodged. Intervention presents risks to the patient and dislodgement can have significant adverse consequences on the patient. Leaving the stent at the implant site permanently also has disadvantages. One drawback of such durably implanted stents is that the permanent interaction between the stent and surrounding tissue can pose a risk of endothelial dysfunction and late thrombosis.

In order to effect healing of a diseased blood vessel, the presence of the stent is necessary only for a limited period of time. The development of a bioresorbable stent or scaffold obviates the permanent metal implant in vessel, allows for late expansive luminal and vessel remodeling, and leaves only healed native vessel tissue after the full absorption of the scaffold. Stents fabricated from biodegradable, bioabsorbable, and/or bioerodable materials such as bioabsorbable polymers can be designed to completely erode only after or some time after the clinical need for them has ended. Consequently, a fully bioabsorbable stent can reduce or eliminate the risk of potential long-term complications and of late thrombosis. However, it is believed that the bioabsorbable stent can still pose a risk of thrombosis during the limited period of time a bioabsorbable stent is present in a vessel.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a bioabsorbable stent comprising: a PLLA scaffolding composed of a plurality of struts having a thickness between 100 and 200 microns and; a first coating layer above all or a portion of the PLLA scaffolding having a thickness less than 5 microns, wherein the coating layer comprises an antiproliferative drug distributed throughout a coating polymer, wherein immobilized antithrombotic agent is at an outer surface of the coating layer, wherein the coating layer is free of the immobilized antithrombotic agent below the outer surface of the coating layer, wherein the antithrombotic agent is selected from the group consisting of heparin, non-adhesive proteins, cell adhesive proteins, cell adhesive peptide sequences, and hydrophilic monomers or polymers.

Further embodiments of the present invention include a bioabsorbable stent comprising: a PLLA scaffolding composed of a plurality of struts having a thickness between 100 and 200 microns and; a first coating layer above all or a portion of the PLLA scaffolding having a thickness of less than 5 microns, wherein the first coating layer comprises a coating polymer with an antiproliferative drug distributed through the coating layer, wherein immobilized antithrombotic agent is distributed throughout the coating layer, wherein the antithrombotic agent is selected from the group consisting of heparin, non-adhesive proteins, cell adhesive proteins, cell adhesive peptide sequences, and hydrophilic monomers or polymers.

Additional embodiments of the present invention include a bioabsorbable stent comprising: a PLLA scaffolding composed of a plurality of struts having a thickness between 100 and 200 microns and; a first coating layer over the PLLA scaffolding having a thickness of less than 5 microns, wherein the first layer is composed of an antiproliferative drug distributed throughout a first coating polymer; a second coating layer above the first coating layer having a thickness of less than 2 microns, wherein the second coating layer comprises a second coating polymer selected from the group consisting of PDLLA and PGLA, wherein immobilized antithrombotic agent is distributed throughout the second coating layer, and wherein the antithrombotic agent is selected from the group consisting of heparin, non-adhesive proteins, cell adhesive proteins, cell adhesive peptide sequences, and hydrophilic monomers or polymers.

Other embodiments of the present invention include a bioabsorbable stent comprising: a PLLA scaffolding composed of a plurality of struts having a thickness between 100 and 200 microns; and at least two coating layers above all or a portion of the PLLA scaffolding, wherein each coating layer has a thickness less than 2 microns, wherein each coating layer comprises a surface eroding polymer, wherein the polymer is selected from the group consisting of hydrophobic aliphatic polyanhydrides, hydrophobic aromatic polyanhydrides, polyester amides, poly(ortho esters), and polyketals, and wherein immobilized antithrombotic agent is at an outer surface of each coating layer.

DETAILED DESCRIPTION OF THE INVENTION

Various embodiments of the present invention relate to a bioabsorbable stent and methods of making thereof for treatment of coronary artery disease. These embodiments include a stent scaffolding with a coating having immobilized antithrombotic agents that reduce or prevent thrombosis prior to endothelialization of the stent. The embodiments further include a stent scaffolding or its coating having immobilized endothelialization-promoting agents.

Coronary artery disease refers to a condition in which the arteries that supply blood to heart muscle become hardened and narrowed or stenotic. This is due to the buildup of cholesterol and other material, called plaque, on their inner walls. Such narrowed or stenotic portions are often referred to as lesions. Coronary artery disease includes restenosis which refers to the reoccurrence of stenosis.

Figure 1:
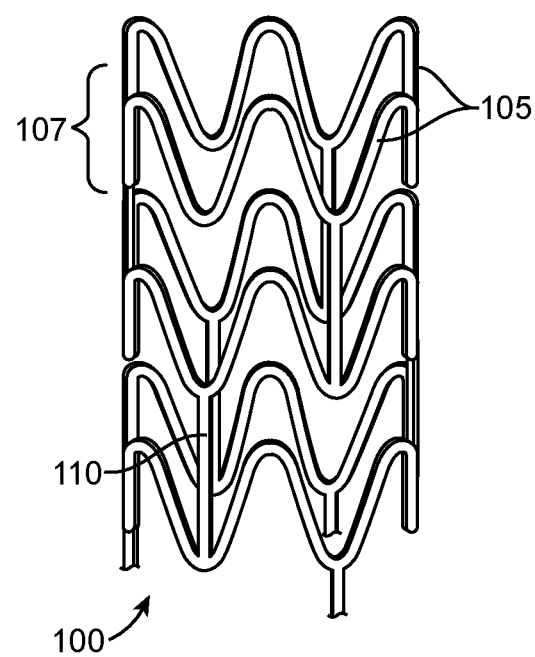
FIG. 1 depicts an exemplary stent scaffolding.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. The cylindrical rings are load bearing in that they provide radially directed force to support the walls of a vessel. The linking elements generally function to hold the cylindrical rings together and do not contribute significantly to the support of the lumen. The structural pattern in FIG. 1 is merely exemplary to illustrate the basic structure of a stent pattern.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

In general, a stent can be made partially or completely from a biodegradable, bioabsorbable, or biostable polymer. A polymer for use in fabricating a stent can be biostable, bioabsorbable, biodegradable or bioerodable. Biostable refers to polymers that are not biodegradable. The terms biodegradable, bioabsorbable, bioresorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

In general, in order to facilitate healing of a diseased section of a vessel, the presence of a stent is necessary for only a limited period of time. Therefore, a stent made from a biodegradable polymer is intended to remain in the body for a duration of time until its intended function of facilitating healing a diseased section of a blood vessel is completed. After the process of degradation, erosion, absorption, and/or resorption has been completed, no portion of the biodegradable stent, or a biodegradable portion of the stent will remain at the treated section of the blood vessel. In some embodiments, very negligible traces or residue may be left behind.

Additionally, the stent can further include a therapeutic coating or layer above all or a portion of the scaffolding. The coating can be composed of a bioabsorable polymer with one or more therapeutic agents dispersed or dissolved in the polymer. The therapeutic agents can include, but are not limited to, antiproliferatives, and anti-inflammatories.

After deployment, the stent maintains patency of the diseased section for a limited period of time until chemical degradation results in degradation of the radial strength to the point that the stent can no longer support the walls of the section of the vessel. The bioabsorbable stent provides patency to the stented segment for a finite period of time, the radial strength of the stent deteriorates, making the stent unable to continue to provide patency to the vessel walls. The loss of radial strength is followed by a gradual decline of mechanical integrity, gradual loss of mass from the stent, and eventually disappearance of the stent from the stented segment. The time dependent radial strength profile of the stent includes an initial period after intervention in which the stent maintains its radial strength to prevent negative remodeling of the vessel which is then followed by a loss of radial strength.

The stent may include a coating to release anitproliferative agent to control restenosis during an initial period caused by smooth muscle cell proliferation (SMP). The drug release declines to zero to allow healing processes to occur. The stent may be designed to provide a release profile which controls proliferation during smooth muscle cell proliferation, but terminates soon enough to allow complete or almost complete endothelialization prior to substantial mass loss and mechanical integrity loss. The drug release profile may decline to zero between 3-4 months after intervention. This allows for endothelialization of stent struts between 4 and 6 months after intervention.

Figure 2A:
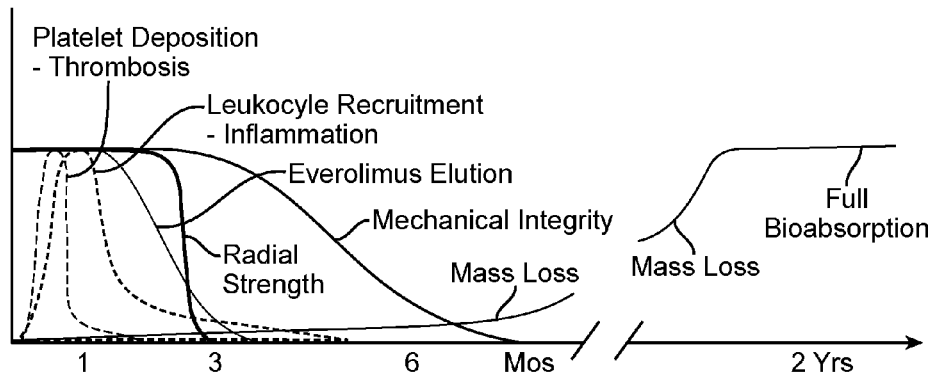
FIGS. 2A-C represent a schematic representation of an exemplary embodiment depicting the properties of an implanted bioabsorbable stent as a function of time.
Figure 2B:
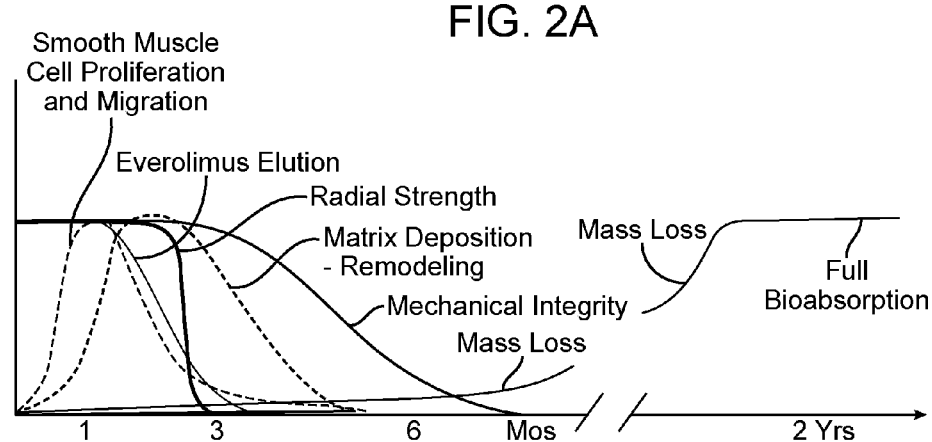
Figure 2C:
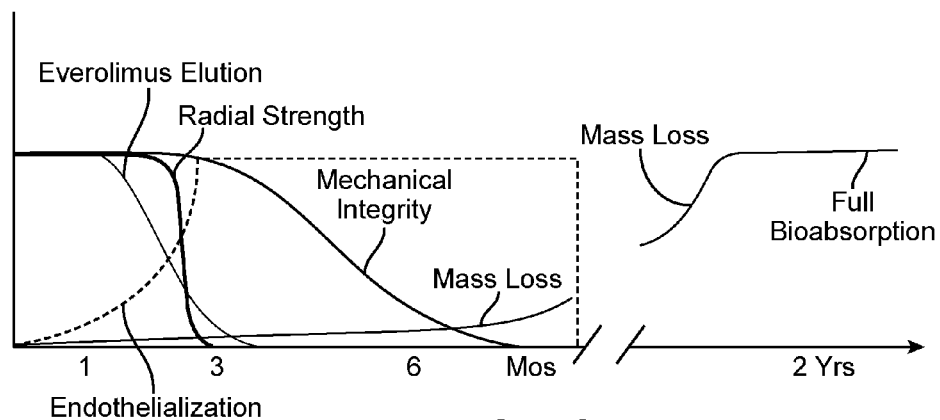

FIGS. 2A-C depict a schematic representation of exemplary time dependent behavior of a bioabsorbable stent after intervention at an afflicted section of a vessel. In addition, FIGS. 2A-C also show expected biological responses of the vessel to the stent as a function of time.

Each of FIGS. 2A-C shows the time dependence of the stent properties, the radial strength, drug release, mechanical integrity, and erosion or mass loss. The radial strength of the stent is maintained for a period of time (in this case, after intervention during which the stent supports the vessel walls. The stent then experiences a rapid deterioration in radial strength, due to molecular weight loss, and can no longer support the lumen walls (in this case, about 3 months after intervention). The drug release is maintained at a relatively constant level after intervention (in this case, between 1-1.5 months after intervention) followed by a relatively rapid decline to zero (in this case, between 3-4 months after intervention). The structural integrity is maintained at a relatively constant level for a period of time after intervention (in this case, about 3-4 months after intervention) followed by a gradual decline until a complete loss at a time greater than 6 months. The period of structural integrity retention is longer than radial strength retention and the rate of decline of mechanical integrity is more gradual.

There are several phases of biological response and vessel changes due to the intervention of the stent. The time period from intervention to about 1-3 months after intervention is referred to as the acute phase. FIG. 2A depicts two biological responses to the stent that occur during this phase, platelet deposition and leukocyte or white cell recruitment. These biological responses can dissipate quickly if there is growth of cellular layers over the stent.

FIG. 2B depicts additional biological responses during the acute phase, smooth muscle cell proliferation (SMP) and matrix deposition. SMP occurs at the inner surface of the vessel wall in the stented section. The exemplary profile in FIG. 2B shows that the smooth muscle cell proliferation reaches a peak between one and two months and then decreases to negligible levels at about five months. Smooth muscle cell proliferation can be explained with reference to the structure of an arterial wall. Smooth muscle cell proliferation is expected to occur during a time period up to about three months after implantation of the stent. Smooth muscle cell proliferation should be controlled since it can lead to restenosis. Therefore, a bioabsorbable stent can release an antiproliferative agent, typically from a therapeutic coating layer over the stent scaffolding to control the smooth muscle cell proliferation. The therapeutic agent release can occur up to two or four months from intervention.

Matrix deposition involves deposition of collagen and elastin in the neointima layer, reinforcing the layer which enables it to provide mechanical support. Matrix deposition is a key component of the remodeling process. Remodeling refers to a biological response that results in modification of the neointima layer formed from smooth muscle cell proliferation that facilitates a restoration of normal function of the vessel.

Endothelialization refers to the formation of a layer of endothelial cells over the neointima layer and the stent. FIG. 2C, which depicts cumulative endothelialization as a function of time, shows that endothelialization starts shortly after implantation and reaches a maximum just before three months. Endothelialization results in formation of hemocompatible surface between the blood flow and the stent. Endothelialization plays a critical role in the healing process with a bioabsorbable stent. Both the degree of endothelialization and timing of the endothelialization with respect to the stent behavior are crucial outputs. Endothelialization of the vessel wall and stent struts is essential to prevent thrombosis associated with blood contacting stent surfaces, incomplete strut apposition (persistent or late-acquired), and dislodgement of stent material when mechanical integrity of the stent fails.

The presence of a blood-contacting surface of a foreign body regardless of the level of hemocompatibility of the bioabsorbable material of the stent, for example, presents the risk of thrombosis. In general, an endothelial layer plays a crucial role in reducing or preventing vascular thrombosis and intimal thickening. Specifically, the endothelial layer reduces or prevents deposition of proteins on the vessel wall or stent struts. Such deposition can contribute to or increase risk of thrombosis. Therefore, early and complete endothelialization of the vessel wall and stent are essential. Complete endothelialization should occur between 4 and 6 months to reduce the risk of or avoid the thrombo-embolitic events associated with incomplete strut apposition and dislodgement of material in the vessel.

The antiproliferative drug release is necessary to avoid restenosis due to acute phase SMP, however, it also interferes with endothelialization. Thus, antiproliferative drug release may be designed to rapidly decline to zero by 3 to 4 months after implantation so as not to interfere with endothelial growth. In a human patient, endothelial layer growth can occur between post-stenting to 3 months, or up to six months, or more than six months after implantation.

Therefore, stent surfaces are in contact with blood during a period after implantation prior to complete endothelization. The degree of contact is initially very high immediately after implantation and decreases with time as endothelialization occurs. During this period there may be an increased risk of thrombosis arising from the contact of the stent with blood. The risk is expected to be greatest in the first 1-2 months after implantation. It would be desirable to reduce this risk of thrombosis prior to complete endothelialization while not interfering with either the control of SMP or endothelialization.

The stents of the present invention include modifications that improve the hemocompatibility of stent during the period prior to endothelialization when the stent may pose a risk of thrombosis due to stent-blood contact. The modifications act synergistically with antiproliferative agents by providing hemocompatibility during and without interfering with antiproliferative agent release. The hemocompatibility provided by the modification may be provided during a limited period of time, for example, during the antiproliferative drug release.

The risk of thrombosis presented by a stent is typically treated systemically with anti-coagulatents. Systemic administration can be accomplished orally or parenterally including intravascularly, rectally, intranasally, intrabronchially, or transdermally. An anticoagulant is a substance that prevents coagulation; that is, it stops blood from clotting. However, systemic anti-coagulent therapy can have side-effects. The most common side effects associated with anticoagulant therapy are itching, rashes, easy bruising, increased bleeding from injuries and purplish spots on the skin. Purplish skin spots are caused by small amounts of bleeding under the skin. Bruising tends to be more severe when taking anticoagulants, and bleeding from wounds can be difficult to stop.

The present invention provides advantages over systemic anti-coagulent therapy. The modifications to the stent may reduce or replace systemic anti-coagulatent therapy. The modifications to the stent that provide hemocompatibility are localized to the implant and can be configured to act only during the limited time that they are needed, thus do not have the side-effects of systemic therapy.

The various embodiments of the present invention include modifications of a bioabsorbable stent scaffold and coatings. The scaffold is composed of a plurality of interconnecting struts. Exemplary biodegradable polymers for use with a bioabsorbable polymer scaffolding include poly(L-lactide) (PLLA), poly(D-lactide) (PDLA), polyglycolide (PGA), and poly(L-lactide-co-glycolide) (PLGA). With respect to PLGA, the stent scaffolding can be made from PLGA with a mole % of GA between 5-15 mol %. The PLGA can have a mole % of (LA:GA) of 85:15 (or a range of 82:18 to 88:12), 95:5 (or a range of 93:7 to 97:3), or commercially available PLGA products identified being 85:15 or 95:5 PLGA.

The fabrication methods of a bioabsorbable stent for use in the methods of treatment described herein can include the following steps:
(1) forming a polymeric tube using extrusion,
(2) radially deforming the formed tube,
(3) forming a stent scaffolding from the deformed tube by laser machining a stent pattern in the deformed tube with laser cutting,
(4) optionally forming a therapeutic coating over the scaffolding,
(5) crimping the stent over a delivery balloon, and
(6) sterilization with e-beam radiation.

In step (2) above, the extruded tube may be radially deformed to increase the radial strength of the tube, and thus, the finished stent. The increase in strength reduces the thickness of the struts required to support a lumen with the stent when expanded at an implant site. In exemplary embodiments, the strut thickness can be 100-200 microns, or more narrowly, 120-180, 130-170, or 140-160 microns.

Detailed discussion of the manufacturing process of a bioabsorbable stent can be found elsewhere, e.g., U.S. Patent Publication No. 20070283552, which is incorporated by reference herein. Embodiments of the present invention include methods of modifying the stent to provide hemocompatibility of the stent, such as, during the anti-proliferative drug release.

The therapeutic coating may include bioabsorbable coating polymer with an antiproliferative agent distributed throughout the coating polymer. A function of the coating polymer is to control the release of the drug. The drug release profile, for example cumulative release vs. time, may be due to both diffusion of the drug out of the polymer and absorption of the coating polymer. The coating polymer may be selected to have a higher degradation rate than the scaffolding polymer to allow for release of the drug over the relatively shorter period of smooth cell proliferation as compared to the time for complete absorption of the scaffolding.

With respect to relative degradation rates of polymers, a first polymer having a "higher" or "faster degradation rate" than a second polymer may refer to the first polymer eroding or absorbing away completely in a shorter period of time than the second polymer. The relative degradation rates may correspond to in vitro degradation or in vivo degradation in an animal or human patient.

The two common erosion mechanisms for degradable polymers are surface and bulk erosion. Ideal surface eroding polymers do not allow water to penetrate into the polymer. Therefore, only a surface layer exposed to moisture undergoes degradation and erosion. Therefore, surface eroding polymers erode layer by layer.

In contrast, bulk eroding polymers have a high uptake of water which diffuses throughout the material during the degradation process. Therefore, bulk eroding polymer degrades and erodes throughout a volume of the material. Therefore, for ideal bulk erosion the total absorption time is independent of the size of the piece degrading, in particular, of the thickness of a coating. However, for actual bulk eroding polymer, the degradation rate does depend on piece geometry and size.

For ideal surface erosion, the erosion rate is directly proportional to external surface area. Thus, for a thin flat slab, for which the external surface area remains constant as the slab becomes progressively thinner, the erosion rate is essentially constant until the polymer is completely eroded. For a surface eroding polymer, control of the time span the polymer persists can be achieved by adjusting the material's dimensions and shape and by changing its chemical properties. (J. A. Tamada and R. Langer, Proc. Natl. Acad. Sci. USA Vol. 90, pp. 552-556, January 1993) Therefore, the total absorption time of a coating depends both on the degradation rate of the polymer at the surface and on the thickness of the coating.

An exemplary stent may include a PLLA scaffold. Exemplary bulk eroding coating polymers for use as a carrier for drugs include PDLLA and PLGA. Both PDLLA and PLGA throughout its LA/GA composition range degrade away faster than the PLLA scaffolding. As shown in by in vitro data Table 1, PLLA is a relatively slow eroding polymer while PDLLA and PLGA are fast degrading.

TABLE 1

Degradation time of bioabsorbable polymers.

| Polymer | Degradation Time (months)[a] |
|---|---|
| PGA | 6-12[1,2] |
| PLLA | >24[1]; >36[2] |
| PDLLA | 12-16[1]; 12-15[2] |
| 85/15 PLGA | 5-6[1] |
| 75/25 PLGA | 4-5[1] |
| 65/35 PLGA | 3-4[1] |
| 50/50 PLGA | 1-2[1] |

[1]Medical Plastics and Biomaterials Magazine, March 1998.
[2]Medical Device Manufacturing & Technology 2005.

Classes of polymers exhibiting surface eroding behavior that can be used for the surface-eroding polymer layer can include, but are not limited to, hydrophobic aliphatic polyanhydrides, hydrophobic aromatic polyanhydrides, polyester amides, poly(ortho esters), and polyketals.

The thickness of coating layers of the present invention may be less than 5 microns, or more narrowly, a thickness of 0.5-1, 1-1.5, 1.5-2, 2.5-3, 3.5-4, 4.5-5, 1-2, 1-3, 2-3, 2-4, or 3-4 microns.

With regard to the discussion of coatings herein, "above" can refer to above a surface, but not necessarily in contact with the surface, such that there are intervening layers between the coating layer and the surface. "Above" can also refer to above the surface and in contact with the surface of the scaffolding.

List Different Classes of Antithrombotic Agents

The modification of the stent to increase hemocompatibility includes antithrombotic agents disposed on the scaffolding or in or on coating layers. Antithrombotic agents include hydrophilic groups, since hydrophilic surfaces in generally have been shown to be more resistant to protein adsorption and may, therefore, reduce the thrombogenicity of a material. Hydrophilic groups can include monomers and polymers of various kinds that are hydrophilic such as 2-hydroxyethylmethacrylate (HEMA), polyethylene glycol methyl ether acrylate (mPEG-acrylate). Any (meth)acrylated hydrophilic monomer or polymer may be used to increase hyrophilicity, including phosphorylcholine methacrylate, hydroxypropylmethacrylate (HPMA), methacrylic acid, N-vinylpyrrolidone, N,N-dimethylacrylamide, beta-carboxyethyl acrylate, N-hydroxyethyl acrylamide, and hydroxypolyethoxy allyl ether.

Antithrombotic agents further include heparin and its derivatives and low molecular weight heparin. Heparin may be immobilized by covalent bonds, such as an amide bond of an amine-containing monomer (e.g. 2-aminoethylmethacrylate) that is grafted to polymer. Heparin may also be immobilized by covalent bonds to amino groups on a polymer. Heparin may also be immobilized by hydrogen bonding.

Various kinds of proteins on the surface of a stent act as endothelialization promoting agents. These proteins include various non-adhesive proteins (e.g. albumin), cell adhesive proteins (e.g. fibronectin), or cell adhesive peptide sequences (e.g. RGD sequence). The proteins may be immobilized by a covalent bond (such as an amide bond) to an ester grafted to a polymer on the stent.

In certain embodiments of the present invention, the proteins may be immobilized on the surface of a scaffolding, such as a PLLA scaffolding. The surface of the scaffolding may be in contact with a bioabsorbable polymer coating that includes an antiproliferative agent. Therefore, as the agent layer absorbs away, the immobilized proteins promote endothelialization as the scaffolding surface becomes a blood-contacting surface. In all of the embodiments discussed below, the scaffolding can optionally include proteins immobilized at its surface to promote endothelialization.

Certain embodiments of the present invention include a coating layer disposed above all or a portion of the scaffolding composed of bioabsorbable polymer, such as PLLA. The coating layer may include a coating polymer with bulk eroding behavior that has a faster degradation rate than the scaffolding polymer. For example, for a scaffolding polymer of PLLA, the coating polymer may be PDLLA and PGLA. In other embodiments, the coating polymer is a surface eroding polymer.

In these embodiments, the coating layer may include a therapeutic agent such as an antiproliferative agent or an anti-inflammatory agent. The agent may be mixed or dispersed throughout the coating layer, and thus, mixed or dispersed throughout the coating polymer. In such embodiments, the therapeutic agent may not be immobilized or chemically (i.e., covalently) bound to the coating polymer. The agent may be free to diffuse through the coating polymer after implantation when in contact with bodily fluids.

In some embodiments, the coating layer may contain only the coating polymer and the antiproliferative drug. In exemplary embodiments, the coating polymer can be between 30-80 wt % or 40-60 wt % of the coating layer. In exemplary embodiments, the agent can be between 30-80 wt % or 40-60 wt % of the coating layer.

When stated herein that a coating layer is free of a substance prior to implantation, the coating layer is free of the substance except for incidental diffusion of the substance into the coating layer prior to implantation.

In some embodiments, the first coating layer includes an immobilized antithrombotic agent. "Immobilized" generally refers to the inability of an agent molecule to diffuse away from a location in or on a substrate material, such as a coating material. In the context of an immobilized agent in or on a bioabsorbable polymer, the agent is incapable of diffusing away from its location in or on the coating material without the chemical breakdown of the biodegradable substrate material that is directly or indirectly preventing the agent from diffusing. Indirect or direct bonding of the immobilized agent to the substrate prevents the agent from diffusing. Thus, the immobilized agent can diffuse away from a substrate such as a coating polymer if the coating material that directly or indirectly binds it to the coating absorbs away. Immobilized can also refer to substantial reduction in the ability of an agent to diffuse away from a location.

Specifically, for both bulk and surface eroding polymers, exposure of the coating to bodily fluids causes hydrophilic degradation of the coating polymer which results in chain scission of the coating polymer. As degradation proceeds, the molecular weight of the species is reduced to a level that the degradation products are soluble in the bodily fluids and are absorbed away.

The immobilization of antithrombotic agents to the coating polymer maintains the presence of the agents in or on the coating layer and thus maintains the hemocompatibility provided by the agents during the critical period of potential risk during drug release. Agents immobilized in or on the coating layer are to be contrasted with agents immobilized in or on durable or nonerodible coatings. Such immobilized agents remain immobilized indefinitely since the coating does not degrade or absorb, at least as long as the mechanism of immobilization remains intact. Thus, in the case of a stent with a nonerodible coating with immobilized agents, the agents are permanent, even after they are no longer needed. In the present invention, the antithrombotic agents may be maintained only as long as they are needed, for example, during antiproliferative drug release or prior to complete endothelialization.

Agents may be immobilized in various ways such as by covalent bonding the agents to molecules of the coating polymer, either directly or indirectly. Agents may be immobilized by hydrogen bonding or ionic bonding between the agent and the coating polymer.

In some embodiments, the antithrombotic agents are immobilized only at an outer surface of the coating layer that is at a blood contacting surface. In such embodiments, the immobilized agents can form a monolayer on the outer surface and do not penetrate into the bulk of the coating layer. In some embodiments, the immobilized agents penetrate into the coating layer, for example, by no more than 100 nm. The immobilized antithrombotic may also extend out from the outer surface of the coating layer agents. The immobilized agents are bound to coating polymer molecules only at the surface of the first coating layer. In such embodiments, the immobilized agents improve the hemocompatibility of the surface. As the polymer degrades, the coating polymer at the surface of the coating layer is absorbed or eroded away along with agents bound to the coating polymer.

When the coating polymer is a surface eroding polymer, the polymer at the surface is eroded away first and the immobilized antithrombotic agent bound to the absorbed surface polymer is also absorbed away. Therefore, the hemocompatibility provided by the antithrombotic agent is limited to the time it takes for the polymer at the surface of the coating polymer to erode away.

This is in contrast to a coating polymer that is bulk eroding which degrades throughout the volume of the coating layer. The antithrombotic agents at the surface thus remain intact for a longer period. An ideal bulk eroding coating layer would exhibit no preferential absorption of polymer at the surface. However, actual behavior may exhibit preferential absorption at the surface resulting in preferential removal of the antithrombotic agent at the surface.

Figure 3:
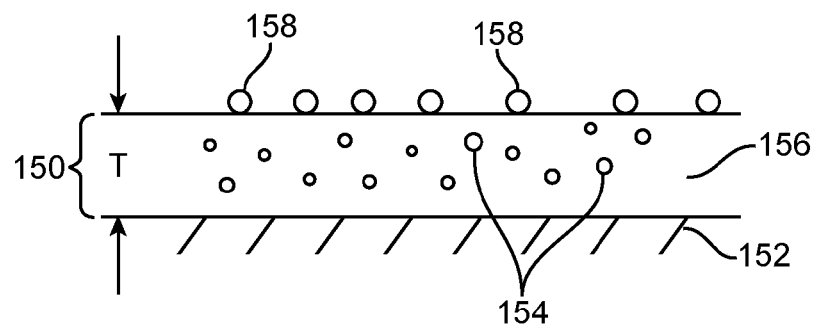
FIG. 3 depicts a cross-section of a surface region of a stent showing a coating layer over a scaffolding with antithrombotic agent immobilized at the surface of the coating layer.

FIG. 3 depicts a cross-section of a surface region of a stent illustrating the embodiments disclosed above. FIG. 3 shows a coating layer 150 disposed over a scaffolding 152. Coating layer 150 has a thickness T. The coating layer includes a coating polymer 156 with antiproliferative agent 154 dispersed throughout the coating layer. The coating polymer may be a bulk eroding or surface eroding polymer. An antithrombotic agent 158 is immobilized at the surface of the coating layer.

In some embodiments, the antithrombotic agent is immobilized and distributed throughout the coating layer between an inner surface and an outer surface of the coating layer. "Inner surface" refers to surface of a coating layer opposite to its outer layer that faces away from a blood contacting surface.

The presence of antithrombotic agent throughout the coating layer would increase the duration of the hemocompatibility provided by the antithrombotic agent for both surface and bulk eroding coating polymers as compared to antithrombotic agent at a surface alone. The increase in duration would be more significant for a surface eroding coating polymer since the surface layer with the agent erodes away first. As the surface eroding coating layer absorbs, antithrombotic agent that was below the surface prior to absorption would be exposed and provide hemocompatibility.

Additionally, the antithrombotic agent throughout the coating layer would increase the duration and degree of hemocompatibility of a bulk eroding polymer as well. This would be expected to be the case even if there is no preferential absorption of coating polymer at the surface. Even with no preferential absorption, coating polymer at the surface absorbs and antithrombotic agent immobilized to the absorbed material is removed. The absorbed material may then expose antithrombotic agent that is distributed below the surface which would then provide hemocompatibility.

Figure 4:
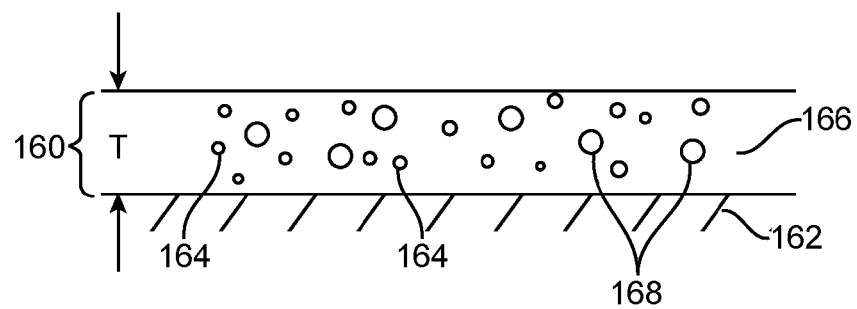
FIG. 4 depicts a cross-section of a surface region of a stent showing a coating layer over a scaffolding with immobilized antithrombotic agent throughout the coating layer.

FIG. 4 depicts a cross-section of a surface region of a stent illustrating an embodiment of the present invention. FIG. 4 shows a coating layer 160 disposed over a scaffolding 162. Coating layer 160 has a thickness T. The coating layer includes a coating polymer 166 with antiproliferative agent 164 (solid circles) dispersed throughout the coating layer. An antithrombotic agent 158 (open circles) is immobilized and distributed throughout the coating layer.

In further embodiments, a first coating layer may be disposed above a bioabsorbable scaffolding made of a polymer such as PLLA. The first coating layer may be above and in contact with the PLLA scaffolding surface without any intervening layers. The first coating polymer may include a first coating polymer that may be a bulk eroding polymer or surface eroding polymer, as described herein. The thickness of the first coating layer may be any of the ranges of thickness disclosed above and other ranges such as less than 5 microns, 2-3 microns, 2.5 to 3.5 microns, or 2.7 to 3 microns.

In these embodiments, the first coating layer may include a therapeutic agent such as an antiproliferative agent or an anti-inflammatory agent. The agent may be mixed or dispersed throughout the first coating layer. In such embodiments, the therapeutic agent may not be immobilized or chemically (i.e., covalently) bound to the first coating polymer. The agent may be free to diffuse through the first coating polymer.

In some embodiments, the first coating layer may contain only the first coating polymer and the antiproliferative drug. The coating layer may be 30-80 wt % or 40-60 wt % of drug. The coating layer may be 30-80 wt % or 40-60 wt % of coating polymer. In some embodiments, the first coating layer is free of antithrombotic agent prior to implantation.

In such embodiments, a second coating layer may be disposed above the first coating layer. The second coating layer may be in contact with an outer surface of the first coating layer with no intervening coating layers between the first and second coating layers. The second coating layer may preferably include or be composed of a bulk eroding polymer such as PDLLA or PLGA. In some embodiments, the second coating layer includes an immobilized antithrombotic agent distributed throughout the second coating layer. In some embodiments, the second coating layer is free of therapeutic agents other than the antithrombotic agent prior to implantation. For example, the second coating layer is free of antiproliferative or anti-inflammatory agents prior to implantation.

When the stent is implanted, the agent in the first coating layer may elute or diffuse through the second coating layer and out of the coating. The antithrombotic agent in the second coating layer provides increased hemocompatibility during the delivery of the agent from the first coating layer. In some embodiments, the first coating polymer is the same as the second coating polymer. For example, both the first and second coating polymer are PDLLA or PLGA with the same composition.

The thickness of the second coating layer can be tailored to facilitate diffusion of therapeutic agent from the first coating layer. For example, the second coating layer may be less than 2 microns or more narrowly between 1-2 microns.

Figure 5:
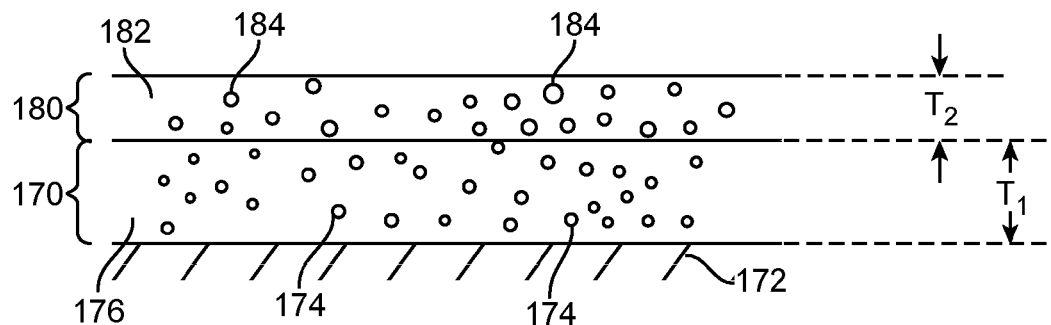
FIG. 5 depicts a cross-section of a surface region of a stent showing two coating layers over a scaffolding with immobilized antithrombotic agent throughout the outer coating layer.

FIG. 5 depicts a cross-section of a surface region of a stent illustrating the embodiments discussed above. FIG. 5 shows a first coating layer 170 disposed over a scaffolding 172. Coating layer 170 has a thickness T1. The first coating layer includes a coating polymer 176 with antiproliferative agent 174 dispersed throughout the first coating layer. FIG. 5 further shows a second coating layer 180 is disposed over the first coating layer 170. Second coating layer 180 has a thickness T2. Second coating layer 180 includes a second coating polymer 182 and an antithrombotic agent 184 that is immobilized and distributed throughout the second coating layer 180.

In additional embodiments, the coating layer can include immobilized proteins on a surface of the coating layer or distributed throughout the coating layer in addition to an antithrombotic agent such as heparin or hydrophilic monomers or polymers that are immobilized at the surface of or distributed throughout the layer. The immobilized proteins would promote endothelialization while the antithrombotic agents would provide hemocompatiblity.

In additional embodiments, at least two coating layers may be disposed above a bioabsorbable scaffolding made of a polymer such as PLLA. In some embodiments, there are no intervening layers in between the coating layers. The innermost layer of the at least two coating layers (i.e., the layer closest to the scaffolding surface) may be in contact with the scaffolding with no intervening layers between the innermost layer and the scaffolding surface.

In some embodiments, at least one of the two coating layers includes an antithrombotic agent immobilized at a surface of or in the coating layer. Each of the coating layers may include an antithrombotic agent. In other embodiments, any combination of the layers may include or be free of an antithrombotic agent.

The antithrombotic agents may be immobilized only at an outer surface of the coating layer. In such embodiments, the immobilized agents can form a monolayer on the outer surface and do not penetrate into the bulk of the coating layer. In some embodiments, the immobilized agents penetrate into the coating layer, for example, by no more than 100 nm.

In such embodiments, the immobilized agents improve the hemocompatibility of the surface of the outermost coating layer. As the polymer degrades, the coating polymer at the surface of the coating layer is absorbed or eroded away along with antithrombotic agents bound to the coating polymer.

In some embodiments, each of the at least two coating layers may include or be composed of a surface eroding polymer. Each of the coating layers may be composed of the same surface eroding polymer. "Same" polymer means that the polymers have the same chemical composition and molecular weight distribution. In other embodiments, the at least two coating layers are made of different polymers. For example, polymers can be selected based on degradation rate. The degradation rate of the coating polymers can increase, decrease, or alternate from the innermost layer to the outermost layer. The relative degradation rate may be adjusted based on a desired release profile of any therapeutic agents included in the coating layers.

In further embodiments, at least one of the at least two coating layers includes a therapeutic agent other than an antithrombotic agent distributed through the coating layers. The therapeutic agent may be an antiproliferative or anti-inflammatory agent. Each of the layers may include the same therapeutic agent. Alternatively, any of the layers may be free of the therapeutic agent.

In some embodiments, the thickness of each of the at least two coating layers may be the same. Alternatively, the thicknesses of the coating layers can differ. The thickness can be selected or adjusted to obtain a desired total absorption time of a coating layer. In exemplary embodiments, the thickness of the at least two layers may be 0.5-1, 0.5-1.5, for 1-2 microns. In some embodiments, the coating layers are relatively thin such as a thickness of the coating layers is 0.1-0.5 microns. Thus, the time between removal of immobilized antithrombotic layers due to surface erosion and exposure of the agents on the surface below is reduced.

Figure 6:
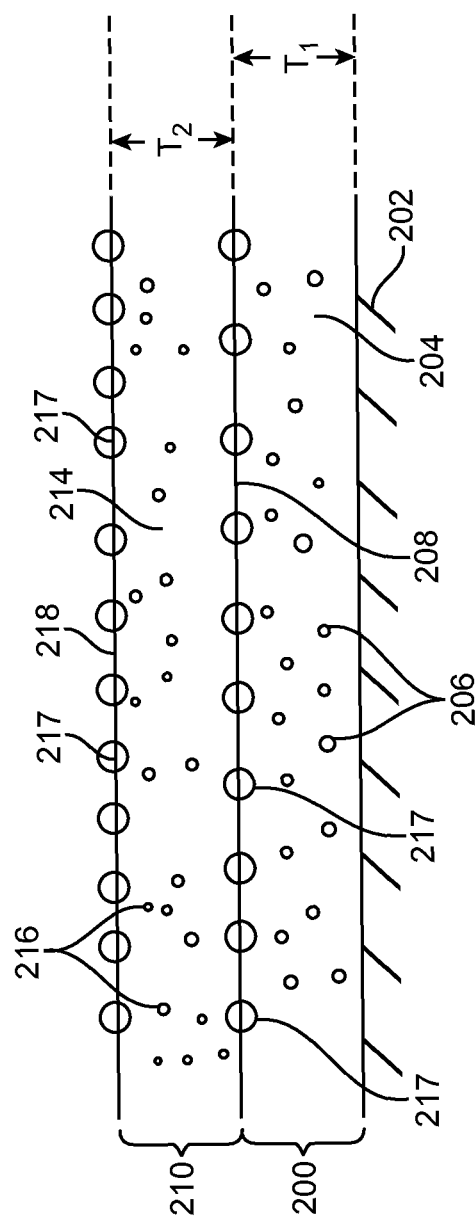
FIG. 6 depicts a cross-section of a surface region of a stent showing two coating layers over a scaffolding with immobilized antithrombotic agent at the surface of each coating layer.

FIG. 6 depicts a cross-section of a surface region of a stent illustrating the embodiments discussed above. FIG. 6 shows a first coating layer 200 disposed over a scaffolding 202. A second coating layer 210 is disposed over first coating layer 200. First coating layer 200 has a thickness T1 and second coating layer 210 has a thickness T2. First coating layer 200 includes a first coating polymer 204 with an antiproliferative agent 206 dispersed throughout the first coating layer. Second coating layer 210 includes a second coating polymer 214 with an antiproliferative agent 216 dispersed throughout the second coating layer. First coating polymer 204 and second coating polymer 214 are surface eroding polymers. An antithrombotic agent 217 is immobilized at a surface 208 of first coating layer 200 and at a surface 218 of second coating layer 210. Upon implantation of a stent of FIG. 6, the immobilized antithrombotic agent would provide increased hemocompatibility while the coating layer erodes and releases antiproliferative agent.

Hydrophilic monomers or polymers may be grafted to a coating polymer surface by applying a coating material including hydrophilic monomer or polymer to the surface of the coating polymer. The coating material can be applied by various known methods such as spraying or dipping. The surface with applied coating is exposed to radiation which generates free radicals in the monomer and coating polymer surface. The highly reactive free radicals result in formation of covalent linkages between the coating polymer and the hydrophilic monomer or polymer.

The coating material includes hydrophilic monomer/polymer dissolved in a solvent. The solvent may be removed either after or before exposure to radiation. The coating polymer may be insoluble in the coating solvent. Alternatively, the coating solvent may be a weak solvent for the coating polymer, the coating solvent may swell the coating polymer, or the coating polymer may be soluble in the coating solvent. Swelling of the coating solvent or dissolution of the coating polymer by the solvent will result in penetration of the immobilized hydrophilic molecules into a surface of the coating polymer. Exemplary solvents include acetone, methyl acetate, ethyl acetate, pentane, toluene, chloroform, diethyl ether, dichloromethane, methanol, isopropanol, and water.

A coating layer that includes immobilized antithrombotic agent distributed throughout the layer can be made by using anitithrombotic agent during preparation of the coating layer. A polymer coating on a scaffolding surface or over another coating layer may be prepared by applying a coating material including the coating polymer and then removing the solvent. The coating material includes the coating polymer dissolved in a solvent. The coating material can further include hydrophilic monomers or polymers dissolved or suspended in solvent and additional therapeutic agent such as antiproliferative and anti-inflammatory agents. The solvent is then removed through evaporation or drying. Typically, a coating layer of a desired thickness is achieved by repeating application and drying steps.

The finished coating layer may then be exposed to radiation which generates free radicals resulting in covalent linkage between the coating polymer and the hydrophilic monomers or polymers. The coating layer may also be exposed to radiation at the end of one or more of the repeated application and drying steps.

An exemplary coating material may include PDLLA dissolved in acetone or chloroform. Hydrophilic monomers or polymers are dissolved in the solvent. An antiproliferative such as everolimus is suspended in the solvent.

Various kinds of radiation may be used to generate free radicals, such as electron beam (E-beam), gamma rays, and X-rays.

The methods for immobilizing hydrophilic monomers and polymers at the surface of a coating layer and throughout the coating layer may be applied to making the embodiments of the stents described herein, for example, as illustrated in FIGS. 3-6.

Heparin may be immobilized in or on a surface of a coating layer in several ways. One technique is to immobilize heparin with amine groups grafted to a coating polymer. An exemplary method of immobilizing heparin on a polymer surface using this technique involves two steps. First, an amine containing (meth)acrylate monomer is grafted to the polymer. A solution of the monomer is applied to coating layer. An amine containing monomer (e.g., 2-aminoethyl-methacrylate) is immobilized on the surface of the coating layer using radiation to activate free radicals on the coating layer surface, which react with the {meth)acrylate groups to form a stable covalent bond between the monomer and the coating polymer surface. The exposure to radiation can be before or after the removal of solvent from the monomer solution of the surface.

Second, the heparin is immobilized onto the amine groups formed in the first step. The carboxylic acid in the heparin can he activated using N-hydroxysuccinimide and 1-Ethyl-3-[3dimethylaminopropyl]carbodiimide (NHS/EDC). Heparin and a solution of NHS/EDC are applied to a surface with grafted monomer. This activated group of heparin will then react with the amine groups on the coating polymer surface to form stable amide linkages between the heparin and the coating polymer.

A coating layer with heparin immobilized throughout the coating layer may be prepared by forming a coating layer containing a coating polymer, (meth)acrylate monomer, heparin, and NHS/EDC. The coating layer may then be exposed to radiation to form the monomers grafted to the coating polymer and the amide linkage between the monomer and the heparin. Alternatively, the first and second steps may be performed at the end of one or more of the repeated application and drying steps used to form a coating layer.

Another technique of immobilizing heparin on a surface of a polymer uses plasma discharge. An exemplary method includes three steps.

First, oxygen plasma glow discharge is used to generate hydroxyl groups on a polymer surface.

Second, a carboxyl or amino group is then introduced on the polymer surface in order to link heparin to the surface:

1. To introduce a carboxyl group, the surface is treated with, e.g., a basic solution and then acidified to form pendant carboxyl groups (—COOH) bonded to surface polymer, for example, PDLLA-COOH.

2. To introduce an amino group, the surface is treated with, e.g., ethylene diamine. This forms pendant amino groups (—NH2) bound to surface polymer, for example, PLLA-NH2.

Third, heparin is immobilized to the carboxylic acid or amino group:

1. Carboxylic acid groups on the heparin are activated with, e.g., 1-ethyl 3-dimethylaminopropyl carbodiimide (EDC). A solution of activated heparin is then applied to the surface with pendant carboxylic groups. Heparin is then immobilized to the activated surface using amino groups on the heparin molecule.

2. Carboxylic acid groups on the heparin arc activated using EDC. A solution of activated heparin is then applied to the surface with pendant amino groups. Activated carboxylic acid groups proceed to immobilize heparin to the amino surface.

A coating layer with heparin immobilized throughout the coating layer may be prepared by performing the three steps at the end of one or more of the repeated application and drying steps used to form a coating polymer layer.

The methods for immobilizing heparin at the surface of a coating layer and throughout the coating layer may be applied to making the embodiments of the stents described herein, for example, as illustrated in FIGS. 3-6.

Proteins may be immobilized on a surface of a scaffolding or coating layer by reaction of the proteins to an ester grafted to the surface. First, an ester in solution such as a hydroxy-succinimide ester containing a reactive acrylate or methacrylate group is applied onto the polymer surface. Before or after removal of the solvent from the applied solution, the surface is exposed to radiation, which is known to form activated free radicals in a polymer. These activated free radicals react with the (meth)acrylate groups on the hydroxysuccinimide ester, forming a covalent bond between the activated ester and the coating polymer.

Second, proteins are then immobilized to the activated surface by reaction of the activated ester with an amine on the protein under slightly alkaline conditions to form an amide bond. This is one example of a method to link amine containing proteins to carboxyl groups on the backbone, however, there are many more ways that are known. These other ways are within the scope of the present invention A coating layer with protein immobilized throughout the coating layer may be prepared by performing the two steps at the end of one or more of the repeated application and drying steps used to form a coating polymer layer.

The methods for immobilizing hydrophilic monomers and polymers at the surface of a coating layer and throughout the coating layer may be applied to making the embodiments of the stents described herein, for example, as illustrated in FIGS. 3-6.

Any drugs having anti-proliferative effects can be used in the present invention. The anti-proliferative agent can be a natural proteinaceous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 known as zotarolimus manufactured by Abbott Laboratories, Abbott Park, Ill.), prodrugs thereof, co-drugs thereof, and combinations thereof.

In one embodiment, the anti-proliferative agent is everolimus. Everolimus acts by first binding to FKBP12 to form a complex (Neuhhaus, P., et al., Liver Transpl. 2001 7(6):473-84 (2001) (Review)). The everolimus/FKBP12 complex then binds to mTOR and blocks its activity (Id.). By blocking mTOR activity, cells are unable to pass through G1 of the cell cycle and as a result, proliferation is inhibited. mTOR inhibition has also been shown to inhibit vascular smooth muscle migration.

Any drugs having anti-inflammatory effects can be used in the present invention. The anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A bioabsorbable stent comprising:
   a poly(L-lactide) (PLLA) scaffolding composed of a plurality of struts having a thickness between 100 and 200 microns; and
   a first coating layer disposed over the PLLA scaffolding and a second coating layer disposed over the first coating layer,
   wherein each coating layer has a thickness less than 2 microns,
   wherein each coating layer comprises a surface eroding polymer,
   wherein the polymer is selected from the group consisting of hydrophobic aliphatic polyanhydrides, hydrophobic aromatic polyanhydrides, polyester amides, poly(ortho esters), and polyketals, and
   wherein immobilized antithrombotic agent is at an outer surface of each coating layer, wherein the immobilized antithrombotic agent is heparin.

2. The stent of claim 1, wherein an antiproliferative agent is distributed throughout each layer.

3. The stent of claim 1, wherein the antithrombotic agent is immobilized only at an outer surface of each coating layer or penetrates into each coating layer by no more than 100 nm.

4. The stent of claim 1, wherein the immobilized antithrombotic agent is immobilized by covalent bonds to the polymer at the outer surface of each coating layer.

5. The stent of claims 1, wherein the antithrombotic agent is immobilized only at an outer surface of each coating layer or penetrates into each coating layer by no more than 100 nm, and wherein the immobilized antithrombotic agent is immobilized by covalent bonds to the polymer at the outer surface of each coating layer.

6. A bioabsorbable stent comprising:
   a poly(L-lactide) (PLLA) scaffolding composed of a plurality of struts having a thickness between 100 and 200 microns; and
   a first coating layer disposed over the PLLA scaffolding and a second coating layer disposed over the first coating layer,
   wherein each coating layer has a thickness less than 2 microns,
   wherein each coating layer comprises a surface eroding polymer,
   wherein the polymer is selected from the group consisting of hydrophobic aliphatic polyanhydrides, hydrophobic aromatic polyanhydrides, polyester amides, poly(ortho esters), and polyketals,
   wherein immobilized antithrombotic agent is at an outer surface of each coating layer,
   wherein an antiproliferative agent is distributed throughout each layer, wherein the antiproliferative agent is selected from the group consisting of rapamycin, structural derivatives and functional analogues of rapamycin, paclitaxel, and taxol.

7. The stent of claim 6, wherein the antithrombotic agent is selected from the group consisting of heparin, non-adhesive proteins, cell adhesive proteins, cell adhesive peptide sequences, and hydrophilic monomers or polymers.

8. The stent of claim 6, wherein the antithrombotic agent is immobilized only at an outer surface of each coating layer or penetrates into each coating layer by no more than 100 nm.

9. The stent of claim 6, wherein the immobilized antithrombotic agent is immobilized by covalent bonds to the polymer at the outer surface of each coating layer.

10. The stent of claim 6, wherein the antithrombotic agent is immobilized only at an outer surface of each coating layer or penetrates into each coating layer by no more than 100 nm, and wherein the immobilized antithrombotic agent is immobilized by covalent bonds to the polymer at the outer surface of each coating layer.

* * * * *